United States Patent
Hershkowitz et al.

(10) Patent No.: US 7,846,401 B2
(45) Date of Patent: Dec. 7, 2010

(54) CONTROLLED COMBUSTION FOR REGENERATIVE REACTORS

(75) Inventors: Frank Hershkowitz, Liberty Corner, NJ (US); Jeffrey W. Frederick, Centreville, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 835 days.

(21) Appl. No.: 11/639,691

(22) Filed: Dec. 15, 2006

(65) Prior Publication Data

US 2007/0144940 A1    Jun. 28, 2007

Related U.S. Application Data

(60) Provisional application No. 60/753,961, filed on Dec. 23, 2005, now abandoned.

(51) Int. Cl.
*C10G 47/00* (2006.01)
(52) U.S. Cl. ........................ 422/198; 422/206; 422/208; 422/211; 422/212; 422/220; 422/223; 208/133; 208/134
(58) Field of Classification Search ............... 208/106, 208/113, 133–134, 146; 422/171, 175, 190, 422/206, 198, 208, 211–212, 220, 223
See application file for complete search history.

(56) References Cited

U.S. PATENT DOCUMENTS 2,313,157 A    3/1943    Linder

| 4,200,682 A | 4/1980 | Sederquist |
| 4,240,805 A | 12/1980 | Sederquist |
| 5,080,872 A * | 1/1992 | Jezl et al. ................... 422/201 |
| 5,710,356 A * | 1/1998 | Subramaniam et al. ..... 585/440 |
| 2003/0235529 A1 * | 12/2003 | Hershkowitz et al. ....... 423/652 |

OTHER PUBLICATIONS

Kolios, G. et al. (2000). Chemical Engineering Science, 55, 5945-5967.*

* cited by examiner

*Primary Examiner*—Glenn A Caldarola
*Assistant Examiner*—Brian McCaig

(57) ABSTRACT

The overall efficiency of a regenerative bed reverse flow reactor system is increased where the location of the exothermic reaction used for regeneration is suitably controlled. The present invention provides a method and apparatus for controlling the combustion to improve the thermal efficiency of bed regeneration in a cyclic reaction/regeneration processes. The process for thermal regeneration of a regenerative reactor bed entails (a) supplying the first reactant through a first channel means in a first regenerative bed and supplying at least a second reactant through a second channel means in the first regenerative bed, (b) combining said first and second reactants by a gas mixing means situated at an exit of the first regenerative bed and reacting the combined gas to produce a heated reaction product, (c) passing the heated reaction product through a second regenerative bed thereby transferring heat from the reaction product to the second regenerative bed.

30 Claims, 6 Drawing Sheets

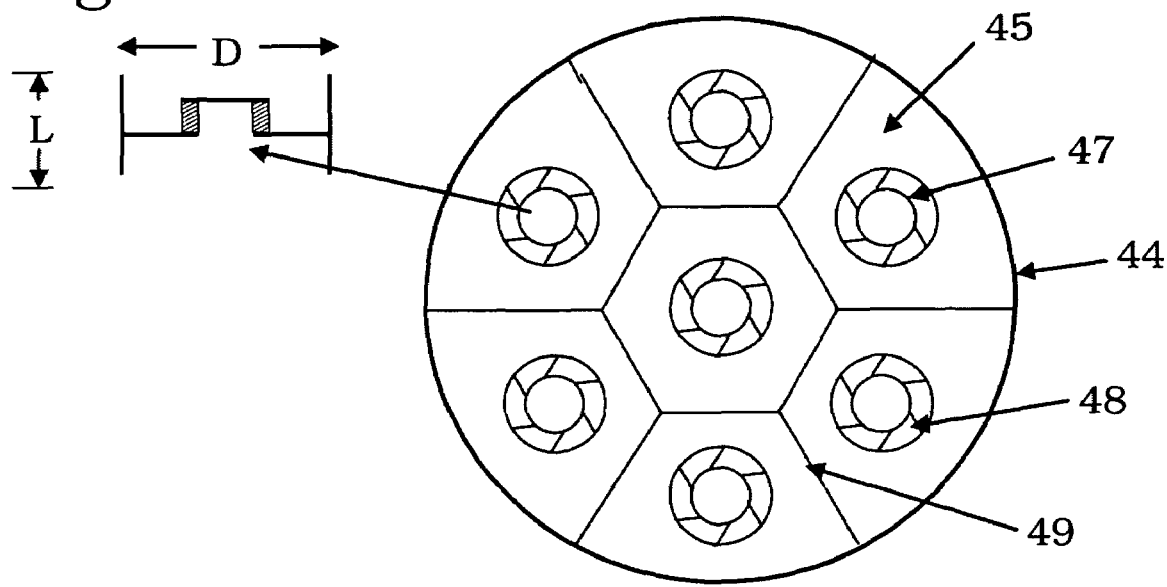

CONTROLLED COMBUSTION FOR REGENERATIVE REACTORS

This application claims the benefit of U.S. Provisional Application No. 60/753,961, filed Dec. 23, 2005.

FIELD OF THE INVENTION

The present invention relates broadly to regenerative reactors. More particularly the invention relates to an improved process and apparatus for controlling combustion for thermal regeneration of reverse flow regenerative reactors in a unique and thermally efficient way.

BACKGROUND OF THE INVENTION

Regenerative reactors are conventionally used to execute cyclic, high temperature chemistry. Typically, regenerative reactor cycles are either symmetric (same chemistry or reaction in both directions) or asymmetric (chemistry or reaction changes with step in cycle). Symmetric cycles are typically used for relatively mild exothermic chemistry, examples being regenerative thermal oxidation ("RTO") and autothermal reforming ("ATR"). Asymmetric cycles are typically used to execute endothermic chemistry, and the desired endothermic chemistry is paired with a different chemistry that is exothermic (typically combustion) to provide heat of reaction for the endothermic reaction. Examples of asymmetric cycles are Wulff cracking and Pressure Swing Reforming.

Conventional regenerative reactors deliver a stream of fuel, oxidant, or a supplemental amount of one of these reactants, directly to a location somewhere in the middle of the regenerative flow path of the reactor, without having that stream pass through regenerative beds or regions. By middle of the regenerative flow path of the reactor, we mean a region of the reverse flow reactor that is in between two regenerative beds or regions, with the main regenerative flow passing from one of these bodies to the other.

In most cases, this stream is introduced via nozzles, distributors, or burners that penetrate the reactor system using a means that is generally perpendicular to flow direction and usually through the reactor vessel side wall. For example, during the exothermic step in a conventional Wulff cracking furnace, air flows axially through the regenerative bodies, and fuel is introduced via nozzles that penetrate the side of the furnace, to combine with air (combusting and releasing heat) in an open zone between regenerative bodies. In a conventional symmetric RTO application, a burner is placed to provide supplemental combustion heat in a location in between two regenerative bodies. The burner combusts fuel from outside the reactor, either with the air passing through the regenerative bodies, or using external air.

Attempts have been made to introduce a reactant of the exothermic step to a location in the middle of the regenerative reactor via conduits that are positioned axially within one or more of the regenerative bodies. For example, Sederquist (U.S. Pat. No. 4,240,805) uses pipes that are positioned axially within the regenerative bed to carry oxidant (air) to locations near the middle of the regenerative flow path.

All of these systems suffer disadvantages. Positioning nozzles, distributors, or burners in the middle of the regenerative flow path of the reactor diminishes the durability of the reactor system. Nozzles, distributors, and burners all rely on carefully-dimensioned passages to regulate flow in a uniform manner, or to create the turbulence or mixing required to evenly distribute the heat that results from the exothermic reaction they support. By function in a regenerative reactor, these nozzles, distributors, are located at the highest-temperature part of the reactor. It is very difficult to fabricate and maintain carefully-dimensioned shapes for use at high temperatures. If the nozzles or distributor loses its carefully-dimensioned shape, it will no longer produce uniform flame temperatures.

A further disadvantage of using nozzles, distributors, or burners to introduce one or more reactant directly into the middle of the regenerative flow path of the reactor is that such an arrangement bypasses that reactant around the regenerative flow path, and thus eliminates the possibility of using the regenerative reactor system to preheat that reactant stream. The fundamental purpose of a regenerative reactor system is to execute reactions at high efficiency by recuperating product heat directly into feeds. Bypassing some fraction of the feed to the reactor around the regenerative system thus reduces the efficiency potential of the reactor system.

It is an object of the present invention to provide a means for operating a regenerative reactor system that alleviates these problems of the conventional design and operation of a regenerative reactor system.

SUMMARY OF THE INVENTION

The present invention provides a method and apparatus for controlling the location of the exothermic reaction used for regeneration in reverse-flow, cyclic reaction/regeneration processes such as pressure swing reforming. The process for thermal regeneration of a regenerative reactor bed entails:
(a) supplying the first reactant through a first channel means in a first regenerative bed and supplying at least a second reactant through a second channel means in the first regenerative bed,
(b) combining said first and second reactants by a gas mixing means situated at an exit of the first regenerative bed and reacting the combined gas to produce a heated reaction product,
(c) passing the heated reaction product through a second regenerative bed thereby transferring heat from the reaction product to the second regenerative bed.

BRIEF DESCRIPTION OF THE DRAWINGS

FIG. 4 is an axial view of gas mixer. FIG. 4a is a cutout cross-sectional view of a portion of FIG. 4.

DETAILED DESCRIPTION OF THE PREFERRED EMBODIMENTS

Figure 1A:
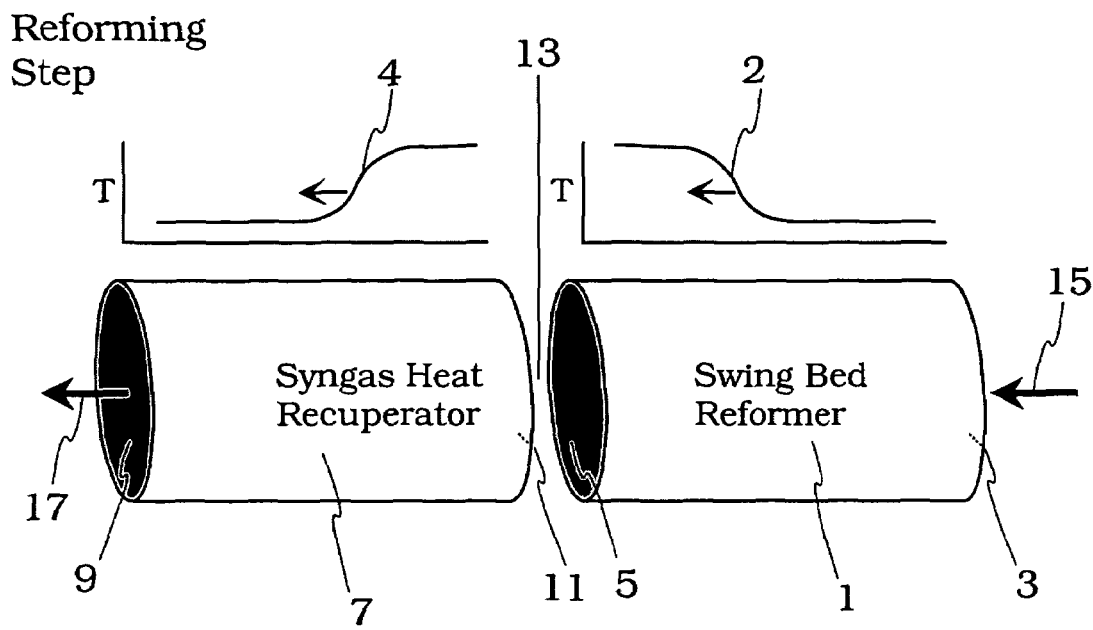
FIG. 1 is a diagrammatic illustration of thermal regeneration in a reverse flow reactor.
Figure 1B:
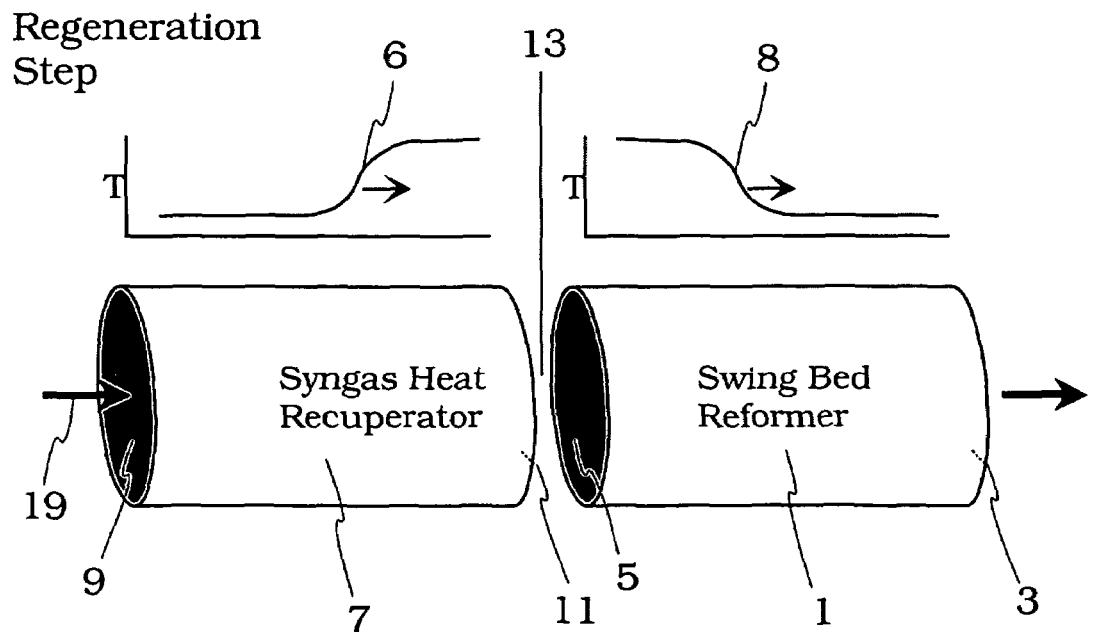

The basic two-step asymmetric cycle of a reverse flow regenerative bed reactor is depicted in FIGS. 1a and 1b in terms of a single bed or reactor having two zones, a first zone, or reaction zone (1) and a second zone, or recuperator zone (7). Both the reaction zone (1) and the recuperator zone (7)

contain regenerative beds. Regenerative beds, as used herein, are intended to comprise material that are effective in storing and transferring heat. The term regenerative reactor bed(s) means a regenerative bed that may also be used for carrying out a chemical reaction. Regenerative beds are generally known in the art and may comprise packing material such as glass or ceramic beads or spheres, metal beads or spheres, ceramic or metal honeycomb materials, ceramic tubes, monoliths, and the like.

As shown in FIG. 1a, at the beginning of the first or "reaction" step of the cycle, the reaction zone (1) is at an elevated temperature and the recuperator zone (7) is at a lower temperature than the reaction zone (1). A reactant feed is introduced via a conduit (15), into a first end (3) of the reaction zone (1).

This feed stream picks up heat from the bed and is reacted, optionally over catalyst, to produce the desired reaction, such as steam reforming, for example. As this step proceeds, a temperature profile (2) is created based on the heat transfer properties of the system. When the bed is designed with adequate heat transfer capability, this profile has a relatively sharp temperature gradient, which gradient will move across the reaction zone (1) as the step proceeds.

Reaction gas exits the reaction zone (1) through a second end (5) at an elevated temperature and passes through the recuperator zone (7), entering through a first end (11) and exiting at a second end (9). The recuperator zone (7) is initially at a lower temperature than the reaction zone (1). As the reaction gas passes through the recuperator zone (7), the gas is cooled to a temperature approaching the temperature of the zone substantially at the second end (9), which is approximately the same temperature as the regeneration feed introduced during the second step of the cycle here illustrated as via conduit (19). As the reaction gas is cooled in the recuperator zone (7), a temperature gradient (4) is created in the zone's regenerative bed(s) and moves across the recuperator zone (7) during this step. The reaction gas exits the recuperator zone at (17). The second step of the cycle, referred to as the regeneration step then begins.

The regeneration step is illustrated in FIG. 1b. Regeneration entails transferring heat from the recuperator zone to the reaction zone to thermally regenerate the reaction beds for the subsequent reaction cycle. Regeneration gas enters recuperator zone (7) here illustrated as via conduit (19), and flows through the recuperator zone and into the reaction zone. In doing so, the temperature gradients (6) and (8) move across the beds similar but in opposite directions to the temperature gradients developed during the reaction cycle. Fuel and oxidant combust at a region proximate to the interface (13) of the recuperator zone (7) and the reaction zone (1). The heat recovered from the recuperator zone together with the heat of combustion is transferred to the reaction zone, thermally regenerating the regenerative reaction beds disposed therein.

In a conventional reverse flow regenerative reactor, fuel and oxidant are typically combined at the combustion zone by injecting either fuel, or oxidant, or both, into the combustion zone, typically via nozzles or injectors through the vessel side walls.

Figure 2:
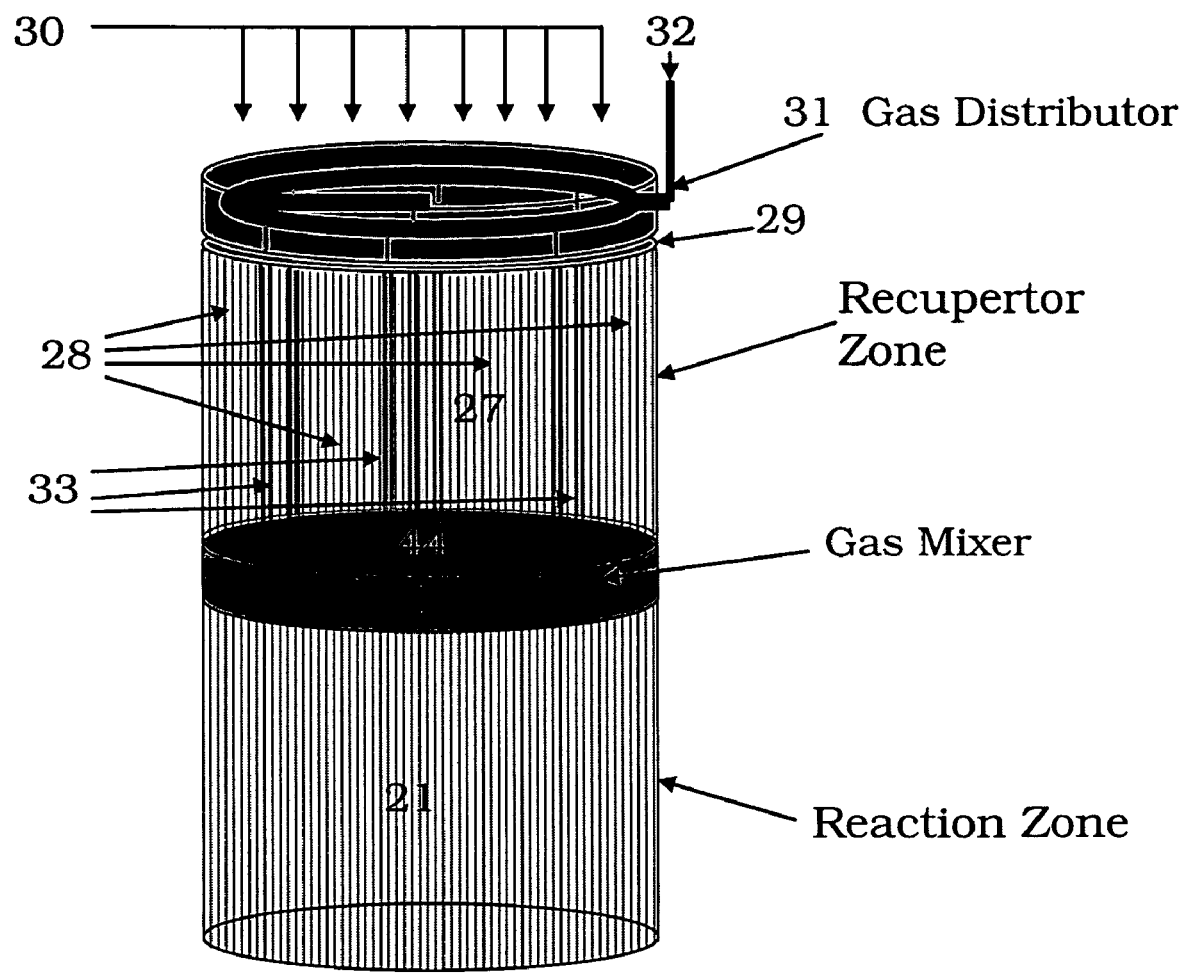
FIG. 2 is a diagrammatic illustration of a regenerative bed reactor with means for controlling the location of the exothermic reaction.

FIG. 2 illustrates means for controlling the combustion of fuel and oxidant to achieve efficient regeneration of the reactor system heat. FIG. 2 depicts a single reactor system, operating in the regeneration cycle.

Referring to the Figure, recuperator zone (27) has gas channel means (28) for channeling two or more gases upon entry to a first end (29) of the recuperator zone (27) through the regenerative bed(s) disposed therein. A first gas (30) enters a first end of a plurality of channel means (28). The gas channel means (28) may comprise channels or tubes or other means suitable for maintaining gases substantially separated from at least a second gas (described hereinafter) while axially transiting the regenerative bed(s) of recuperator zone (27). A gas distributor (31) directs a second gas stream (32) to select channels, here illustrated as channels (33). The result is that at least a portion of gas stream (33) is kept separate from gas stream (30) during its axial transit of the recuperator zone (27). In a preferred embodiment, the regenerative bed(s) of the recuperator zone comprise the channel means. Thereby, the at least two gases that transit the channel means are transiting the regenerative bed(s).

As used in the present invention, gases (30) and (32) comprise two reactants that result in an exothermic reaction when combined, for example a fuel gas and an oxidant gas that result in combustion when combined. By keeping these reactants substantially separated, the present invention controls the location of the heat release that occurs due to exothermic reaction. By "substantially separated", we mean that at least 50%, and preferably at least 75% of the reactant in the first gas (30) has not become consumed by reaction with the second gas (32), and that at least 50%, and preferably at least 75% of the reactant in the second gas (32) has not become consumed by reaction with the first gas (30), by the point at which these gases have completed their axial transit of the recuperator zone (27). In this manner, the majority of the first gas (30) is kept isolated from the majority of the second gas (32), and the majority of the heat release from the reaction of combining gases (30) and (32) will not take place until the gases have exited from the recuperator zone (27). In a preferred embodiment, the channel means structure of recuperator zone (27) comprise a plurality of individual channels oriented substantially parallel to the direction of flow. Such channel structures are provided, for example, by regenerative beds comprised of extruded honeycomb monoliths, or comprised of stacked layers of corrugated materials, as is known in the art. Such channel structures provide a high level of separation of gases in one channel from the next. Alternatively, the regenerative beds of the recuperator zone may comprise packing material or a porous ceramic monolith that is structured to provide substantial separation of the gases (30) and (32).

In a preferred embodiment, the channel means (28) and (33) comprise materials that provide adequate heat transfer capacity to create the temperature profiles (4) and (8) illustrated in FIG. 1 at the space velocity conditions of operation. Adequate heat transfer rate is characterized by a heat transfer parameter $\Delta T_{HT}$, below about 500° C., more preferably below about 100° C. and most preferably below about 50° C. The parameter $\Delta T_{HT}$, as used herein, is the ratio of the bed-average volumetric heat transfer rate that is needed for recuperation, to the volumetric heat transfer coefficient of the bed, $h_v$. The volumetric heat transfer rate (e.g. cal/cm³ sec) that is sufficient for recuperation is calculated as the product of the gas flow rate (e.g. gm/sec) with the gas heat capacity (e.g. ca./gm ° C.) and desired end-to-end temperature change (excluding any reaction, e.g. ° C.), and then this quantity divided by the volume (e.g. cm³) of the recuperator zone (27) traversed by the gas. The $\Delta T_{HT}$ in channel means (28) is computed using gas (30), channel means (33) with gas (32), and total recuperator zone (27) with total gas. The volumetric heat transfer coefficient of the bed, $h_v$, is known in the art, and is typically calculated as the product of a area-based coefficient (e.g. cal/cm²s° C.) and a specific surface area for heat transfer ($a_v$, e.g. cm²/cm³), often referred to as the wetted area of the packing.

In a preferred embodiment, channel means (28) and (33) comprise ceramic channels or tubes, capable of withstanding temperatures exceeding 600° C., more preferably 1000° C., and most preferably 1300° C. Most preferably, channel means (28) comprise a ceramic honeycomb, having channels running the axial length of the recuperator zone (27).

The recuperator zone (27) may include packed bed or foam monolith materials (not shown) that allow dispersion of reactants perpendicular to flow direction, so long as radial dispersion is low enough to keep reactants substantially separated during pass through the recuperator. Calculation of radial dispersion and mixing in bed media is known in the art.

Figure 3:
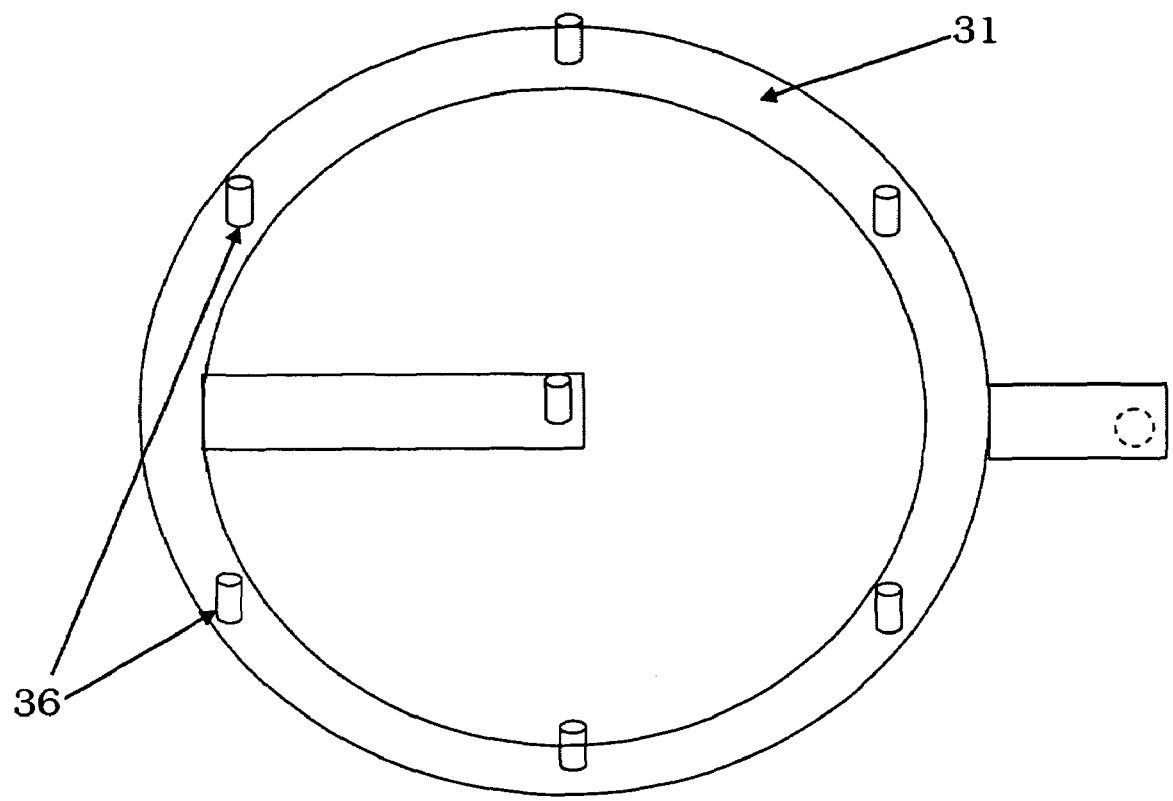
FIG. 3 illustrates an axial view of a gas distributor.

Referring momentarily to FIG. 3, there is shown an axial view of a gas distributor (31) having apertures (36). Referring to both FIGS. 2 and 3, apertures (36) direct the second gas (32) preferentially to select channels (33). In a preferred embodiment, apertures (36) are aligned with, but are not sealed to, the openings of select channels (33). Nozzles or injectors (not shown) may be added to the apertures (36) that are suitably designed to direct the flow of the second gas (32) preferentially to the select channels (33). By not "sealing" the gas distributor apertures (36) (or nozzles/injectors) to the select channels (33), these channels may be utilized during the reverse flow or reaction cycle, increasing the overall efficiency of the system. This "open" gas distributor (31) is also preferred over a "closed" system to facilitate adaptation to multiple reactor systems, where the reactor/recuperator beds may rotate in and out of a gas stream for processing.

The first gas (30) and second gas (32) transit the recuperator zone (27) via channels (28) and (33). Heat, stored in the recuperator zone from the previous cycle, is transferred to both the first and second gas(es). The heated gases are then introduced into gas mixing means (44).

Gas mixing means (44), located between the recuperator zone (27) and the reaction zone (21), functions to mix gas stream (30) and (32), at or near the interface of the reaction zone (21) and the gas mixer means (44).

The mixer means (44) is constructed or fabricated of a material able to withstand the high temperatures expected to be experienced in the reaction zone. In a preferred embodiment, mixer means (44) is constructed from a material able to withstand temperatures exceeding 600° C., more preferably 1000° C., and most preferably 1300° C. For steam reforming of methane, for example, reaction zone temperatures typically exceed 1000° C. In a preferred embodiment, mixer means (34) is constructed of ceramic material(s) such as alumina or silicon carbide for example.

Referring to FIG. 4, there is shown an axial view of one configuration of the gas mixing means (44) together with a cut-away view 4a of one of swirl-mixer means (47).

The gas mixer means (44) shown here comprises sections (45) having swirl mixer means (47) located within the sections (45). In a preferred embodiment, sections (45) are substantially equal in cross sectional area, and swirl mixer means (47) are centrally located within the sections (45).

Gas mixer sections (45) are positioned to segment the gas flow of a plurality of gas channel means (28) and (33). In a preferred embodiment, sections (45) have substantially equal cross sectioned area to facilitate intercepting gas flow from a substantially equal number of gas channel means (28) and (33). Also in a preferred embodiment, gas channel means (28) and (33) are distributed within recuperator (27) such that each of the sections (45) intercepts gas flow from a substantially equal fraction of both first gas channel means (28) and second gas channel means (33). Expressed mathematically, one can define $f_{Ai}$ as the fraction of total cross sectional area encompassed by section i, $f_{28i}$ as the fraction of total channel means (28) intercepted by section i, and $f_{33i}$ as the fraction of total channel means (33) intercepted by section i. In a preferred embodiment, for each section i, the values $f_{28i}$, and $f_{33i}$ will be within about 20% of (i.e. between about 0.8 and 1.2 times the value of) $f_{Ai}$, and more preferably within about 10%. One can further define $f_{30i}$ as the fraction of gas stream (30) intercepted by section i, and $f_{32i}$ as the fraction of gas stream (32) intercepted by the section i. In a more preferred embodiment, for each section i, the values of $f_{30i}$, and $f_{32i}$ will be within about 20% of $f_{Ai}$, and more preferably within about 10%.

Referring momentarily to FIG. 4a, there is shown a cut out section of an individual gas mixer section (45) with swirl mixer means (47). While the present invention may utilize a gas mixer means known to the skilled artisan to combine gases from the plurality of gas channel means (28) and (33), a preferred embodiment of this invention minimizes open volume of the gas mixer means (44) while maintaining sufficient mixing and distribution of the mixed gases. The term open volume means the total volume of the swirl mixers (47) and gas mixer section (45), less the volume of the material structure of the gas mixer. Accordingly, gas mixer section (45) and swirl mixer means (47) are configured to minimize open volume while concurrently functioning to provide substantial gas mixing of the gases exiting gas channel means (28) and (33). In a preferred practice of the invention, gas mixer segment (45) dimensions L and D, are tailored to achieve sufficient mixing and distribution of gases (31) and (32) while minimizing open volume. Dimension ratio L/D is preferably in the range of 0.1 to 5.0, and more preferably in the range of 0.3 to 2.5. For general segments of area A, a characteristic diameter D can be computed as $2(A/\pi)^{1/2}$.

In addition, the total volume attributable to the gas mixer (44) is preferably tailored relative to the total volume of the recuperator bed and reforming bed. Gas mixer (44) preferably has a total volume less than about 20%, and more preferably less than 10% of the combined volume of the recuperator zone (27), reaction zone (21) and the gas mixer means (44).

Referring again to FIG. 2, the gas mixer means (44) so configured combines gases from channels (33) and (28), and redistributes the combined gas across and into reaction zone (21).

In a preferred embodiment, first and second gases comprise fuel and oxidant. Fuel may comprise hydrogen, carbon monoxide, hydrocarbons, oxygenates, petrochemical streams, or mixtures thereof. Oxidant typically comprises a gas containing oxygen, commonly mixed with $N_2$ as in air. Upon mixing the fuel and oxidant at gas mixer (44), the gases combust, with a substantial proportion of the combustion occurring proximate to the entrance to the reaction zone (21).

The combustion of the fuel and oxygen-containing gas proximate to the entrance of the reaction zone creates a hot fluegas that heats (or re-heats) the reaction zone (21) as the flue gas travels across that zone. The composition of the oxygen-containing gas/fuel mixture is adjusted to provide the desired temperature of the reaction zone. The composition and hence temperature is adjusted by means of the proportion of combustible to non-combustible portions of the mixture. For example, non-combustible gases such as $H_2O$, $CO_2$, and $N_2$ can be added to the mixture to reduce combustion temperature. In a preferred embodiment, non-combustible gases comprise steam, flue gas, or oxygen-depleted air as at least one component of the mixture. The hot combustion product passes through reaction zone. The flow of combustion product establishes a temperature gradient within the reaction zone, which gradient moves axially through the reaction zone. At the beginning of the regeneration step, this outlet temperature will be substantially equal (typically within 25° C.) to the inlet temperature of the reforming feed of the preceding, reforming, step. As the regeneration step proceeds, this outlet temperature will increase slowly and then rapidly as the temperature gradient reaches the end of the reforming bed, and can be 50-500° C. above the temperature of the reaction feed by the end of the step.

The controlled combustion reverse flow regenerative reactor system described herein is particularly well suited for steam reforming reactions such as Pressure Swing Reforming as described in U.S. Patent application 2003/0235529A1.

FIG. 1 may be used to illustrate its application to Pressure Swing Reforming. At the beginning of the first step of the cycle, also called the reforming step, the reforming zone (1) is at an elevated temperature and the recuperating zone (7) is at a lower temperature than the reforming zone (1). A hydrocarbon-containing feed may be introduced via a conduit (15), into a first end (3) of the reforming zone (1) along with steam. The hydrocarbon may be any material that undergoes the endothermic steam reforming reaction including methane, petroleum gases, petroleum distillates, kerosene, jet fuel, fuel oil, heating oil, diesel fuel and gas oil, gasoline and alcohols. Preferably, the hydrocarbon will be a gaseous material comprising methane and/or hydrocarbons that are in a gaseous state at the temperature and pressure of the reactor. Preferably, the steam will be present in proportion to the hydrocarbon in an amount that results in a steam to carbon ratio between about 1 and about 3 (considering only carbon in the hydrocarbon, not carbon in CO or $CO_2$ species that may be present).

This feed stream picks up heat from the bed and is converted over the catalyst and heat to synthesis gas. As this step proceeds, a temperature profile (2) is created based on the heat transfer properties of the system. When the bed is designed with adequate heat transfer capability, as described herein, this profile has a relatively sharp temperature gradient, which gradient will move across the reforming zone (1) as the step proceeds.

Synthesis gas exits the reforming bed (1) through a second end (5) at an elevated temperature, passes through mixer (44), as shown in FIG. 2, and then passes through the recuperating zone (7), entering through a first end (11) and exiting at a second end (9). The recuperating zone (7) is initially at a lower temperature than the reforming zone (1). As the synthesis gas passes through the recuperating zone (7), the synthesis gas is cooled to a temperature approaching the temperature of the zone substantially at the second end (9), which is approximately the same temperature as the regeneration feed introduced during the second step of the cycle via conduit (19) (e.g., from about 20° C. to about 600° C.). As the synthesis gas is cooled in the recuperating zone (7), a temperature gradient (4) is created and moves across the recuperating zone (7) during this step.

At the point between steps, the temperature gradients have moved substantially across the reforming zone (1) and the recuperating zone (7). The zones are sized so that the gradients move across both in comparable time during the above reforming step. The recuperating zone (7) is now at the high temperature and the reforming zone (1) is at low temperature, except for the temperature gradient that exists near the exits of the respective zones. The temperature of the reforming zone (1) near the inlet end (3) has now been cooled to a temperature that approaches the temperature of the hydrocarbon feed that has been entering via conduit (15) (e.g., from about 20° C. to about 600° C.).

After the synthesis gas is collected via an exit conduit (17) at the second end (9) of the recuperating zone (7), the second step of the cycle, also called the regeneration step begins. The regeneration step, illustrated in FIG. 1b, basically involves transferring the heat from the recuperator bed (7) to the reformer bed (1) and an exothermic reaction at the interface (13). In so doing, the temperature gradients 6 and 8 move across the beds similar to but in opposite directions to gradients 2 and 4 during reforming. A regeneration gas comprising an oxygen-containing gas and fuel are introduced into the second end (9) of the recuperating zone (7). As described in reference to FIG. 2, the oxygen containing gas is channeled through the recuperator zone substantially separated from the fuel. The fuel and oxidant are combined by means of mixer (44) at interface (13), combusting substantially at the interface of the recuperator zone (7) and the reaction zone (1). Combustion occurs at a region proximate to the interface (13) of the recuperation zone (7) and the reforming zone (1). The term, "region proximate", in the present invention, means the region of the PSR beds in which regeneration step combustion will achieve the following two objectives: (a) the heating of the reforming zone such that end (5) of the reforming zone is at a temperature of at least 800° C., and preferably at least 1000° C. at the end of the regeneration step; and (b) the cooling of the recuperation zone to a sufficient degree that it can perform its function of accepting synthesis gas sensible heat in the subsequent reforming step. Depending on specific regeneration embodiments described herein, the region proximate to the interface can include from 0% to about 50% of the volume of the recuperation zone (7), and can include from 0% to about 50% of the volume of the reforming zone (1). In a preferred embodiment of the present invention, greater than 90% of the regeneration step combustion occurs in a region proximate to the interface, the volume of which region includes less than about 20% the volume of the recuperating zone (7) and less than about 20% the volume of reforming zone (1).

The reforming zone is now, once again, at reforming temperatures suitable for catalytic reforming.

EXAMPLE 1

The following is an example of an asymmetric reverse-flow reactor system used to perform methane steam reforming. The reactor is used in the orientation shown in FIG. 2, with the endothermic reforming step flowing upwards through the reactor (not shown) and exothermic fuel combustion step flowing downwards through the reactor (as illustrated). The diameter of the reactor (inside of insulation) is 2.5 inches. The bed components have diameters of about 2.5 inches to fit within the insulation. The reforming or reaction zone (21) is comprised of a 2.5 inch length of 400 cells/in$^2$ honeycomb that has been wash-coated with reforming catalyst.

The recuperator zone (27) was constructed of several lengths of uncatalyzed 400 cells/in$^2$ honeycomb located at the inlet end that are stacked for a combined height of 1.19 inches.

A distributor means (31) illustrated in FIGS. 2 and 3 was located above the recuperator honeycomb. It comprised a 1.8 inch diameter ring of 0.25 inch (OD) stainless steel tubing with one spoke of tubing extending to the center, and seven metering orifices sized at 0.034 inch ID manufactured on the lower side of the ring; one in the middle on the spoke and six spaced equally around the ring. During the regeneration cycle, the orifices in the ring release the fuel (32) in seven streams located approximately over the centers of each of the channel means (33) (and thereby) the seven mixer segments. Combustion air (30) flowed down around distributor (31) from above into channel means (28).

After transiting the recuperator zone, gases (30) and (32) were combined by gas mixer (44). The mixer (44) was constructed as illustrated in FIG. 4, with seven segments; one central and six around the perimeter. Length of divider (49) was set at about 0.73 inches, to provide for equal cross-sectional area in the seven segments. Segment height (L) was 0.375 inches, while segment characteristic (D) was 0.95 inches, resulting in a segment L/D of about 0.40. A 0.500 inch length region of 0.125 inch inert alumina beads is interposed between the gas mixer and the upper end of the reaction zone to further disperse the mixed gases.

Because the mixer (44) was designed to have equal segment areas, the $F_{Ai}$ value for each of the seven segments was 1/7 or 14.3%. Since each distributor orifice principally feeds one segment, the values for $F_{33i}$ were defined by the performance of the distributor. Prior to operation, the performance of the distributor (31) was measured outside of the reactor. The $F_{33i}$ values for the distributor were: 15.5% for the center orifice, and 13.9%, 14.5%, 14.1%, 14.1%, 13.8%, 14.3% for the six orifices around the ring. This represents a maximum deviation from $F_{Ai}$ of 8.3%.

Valves above and below the reactor were used to control the alternating flows of the reverse-flow operation. The reverse-flow reactor system was run with the following cycle: 15 seconds of regeneration consisting of a flow of oxidant (30) comprising 46.8 SLM air and 137. SLM nitrogen and a flow of fuel (32) comprising 16 SLM of hydrogen; followed by 13.5 seconds of reforming (upflow) comprising 11.9 SLM of methane and 28.2 SLM of steam; followed by 1.5 seconds of product purge (upflow) comprising 28.2 SLM of steam. The regeneration cycle was operated at about 1.7 atm abs, and the reform cycle at 2.0 atm abs. All streams are fed to the reactor at a temperature of about 250° C.

Figure 6A:
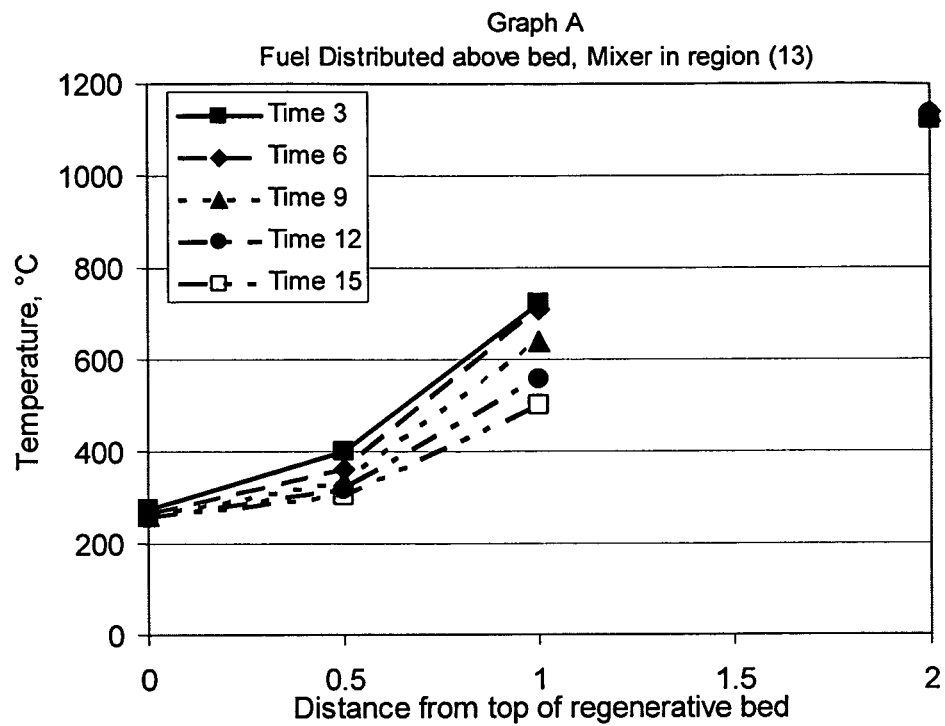
FIG. 6a is a graph of temperature versus distance from the top of the regenerative bed for an embodiment of the present invention.

The reverse flow reactor was operated in this configuration with flows described above, and temperatures were measured at five consecutive times during the regeneration step, at three locations within the recuperator zone (27) and one location proximate to the interface (13) between recuperation and reforming zones, all as measured from the top of the first regenerative honeycomb monolith bed within recuperator zone (27). Temperature measurements are shown in FIG. 6a.

Figure 6B:
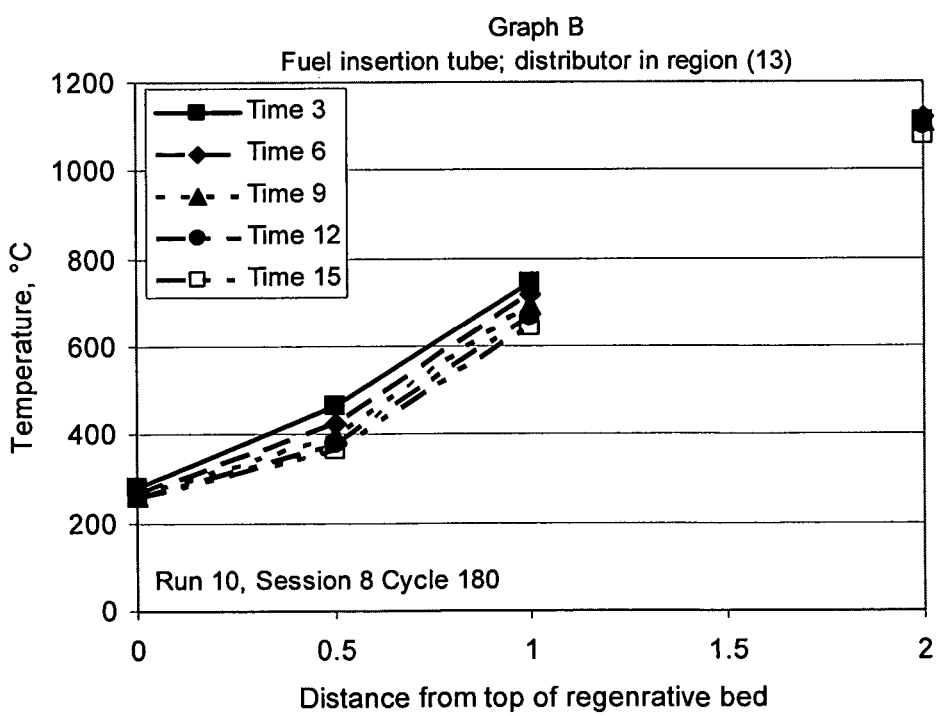
FIG. 6b is a graph of temperature versus distance from the top of the regenerative bed for a fuel insertion device.

A comparative example was performed using a fuel insertion tube coupled to a fuel distributor disk, located in between the reforming and recuperating zones, in lieu of the gas distributor, channel means and gas mixer. For this example, the bottom 0.19 inches of the recuperator zone (27) was replaced with a 0.5 inch long regenerative bed containing 0.125 inch diameter alumina spheres. So configured, the comparative example fuel insertion tube and distributor injected fuel gas to the region between the recuperator zone (27) and the reformer zone (21). The apparatus of the comparative example was operated substantially identical to the above Example, with substantially similar temperature measurements shown in FIG. 6b.

The controlled combustion system described herein may be employed for other, asymmetric reverse flow regenerative reactor systems. The regeneration (exothermic) step, described with respect to FIG. 1B and FIG. 2, can be combustion, as described above for pressure swing reforming, or can other exothermic reactions such as partial oxidation. As applied to partial oxidation, the streams that are fed during the exothermic step comprise a hydrocarbon-containing stream, and a stream with sub-stoichiometric amount of oxidant. By sub-stoichiometric, we mean less oxidant than would be needed to fully oxidize the hydrocarbon-containing stream. These two streams would be maintained substantially separated as described in respect of FIG. 2 above. Typically the stream that has the lesser flow rate will be fed as stream (32), and the greater as stream (30). The endothermic reaction step can be steam reforming, as described above for pressure swing reforming, or can be other endothermic reactions. During the endothermic reaction step, as described with respect to FIG. 1A, the endothermic reactant is fed via conduit 15, is heated and reacted in reaction zone (1), is cooled in recuperation zone (7), with reaction products being collected via conduit (17). Catalyst may be used in one or both zones to facilitate reaction. Preferred endothermic reactions for use with the present invention include steam reforming, dry ($CO_2$) reforming, pyrolysis, catalytic cracking, dehydrogenation, and dehydration. Preferred pyrolysis reactions for use with the present invention include steam cracking reactions such as ethane, naphtha, or gas oil cracking, hydropyrolysis reactions such as methane hydropyrolysis to acetylene, and non-hydrocarbon cracking reactions such as H2S pyrolysis to hydrogen and sulfur. Preferred dehydrogenation reactions for use with the present invention include alkane dehydrogenations such as propane dehydrogenation and alkyl-aromatic dehydrogenations such as ethyl benzene dehydrogenation. Preferred dehydration reactions for use with the present invention include methanol and ethanol dehydration.

EXAMPLE 2

Figure 5A:
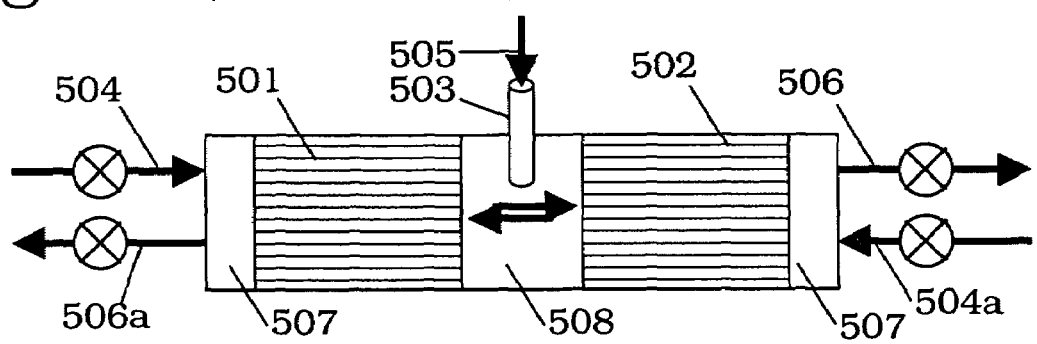
FIG. 5a is a diagrammatic illustration of a conventional Regenerative Thermal Oxidation Reactor; 5b is an illustration of a RTO Reactor with controlled combustion.

The controlled combustion reverse flow regenerative reaction may be employed for Regenerative Thermal Oxidation ("RTO") processes. The RTO processes are conventionally used to combust relatively low levels of contaminants from a larger stream of air. FIG. 5a illustrates the conventional configuration of an RTO reactor, FIG. 5b a RTO reverse flow reactor with controlled combustion.

Referring to FIG. 5a, the process is generally comprised of two regenerative bodies (501, 502) with a burner (503) in between. Contaminated air (504) is heated in the first regenerative body (501), supplemental heat is provided by the combustion of fuel (505) in burner (503) situated between the two regenerative bodies, and the products are cooled to exit the second regenerative body as clean air (506). Frequent flow reversal, switching to streams (504a & 506a), is used to keep the sensible heat (of heating or cooling) moving back and forth between the two bodies (501, 502). All or part of the regenerative bed system (501, 502) may include catalyst in to improve the incineration of the contaminants. Typically, the RTO system includes distribution volume (507) at the cold entry of each regenerative body, and an open volume (508) in which the burner-driven combustion occurs.

Figure 5B:
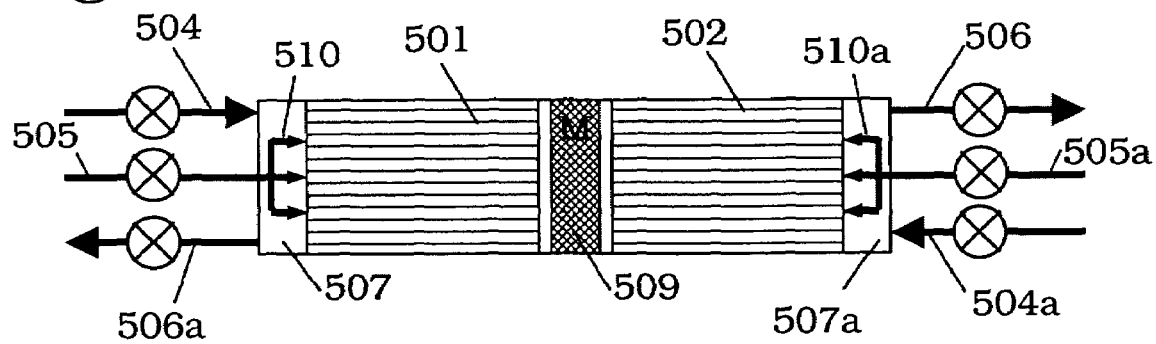

Referring now to FIG. 5b in the present invention, the two regenerative bodies (501, 502) are constructed with packing having substantially parallel channels, and those channels are oriented substantially co-axial with the direction of flow. In between the two regenerative bodies is located the mixing device (509). Contaminated air (504) is heated in the first regenerative bed. Fuel distribution means (510), located in the distribution volume (507) at the cold entry of each regenerative bed, places supplemental fuel (505) into a select number of channels within the regenerative body. This fuel is heated in the first regenerative body and is then mixed with the heated contaminated air in the mixer (509) resulting in combustion and release of heat into the stream. Combustion products are cooled to exit the second regenerative bed as clean air (506). Frequent flow reversal, switching to streams (504a, 510a, 507a, 505a, 506a), is used to keep the sensible heat (of heating or cooling) moving back and forth between the two bodies. All or part of the regenerative bed system (501, 502) may include catalyst to improve the incineration of the contaminants.

As illustrated, there does not need to be a seal between the distributor (510) and the regenerative body (501). Combustion will not occur until gases have been heated which heating occurs during its transit of the recuperator zone. As long as the majority of the fuel is isolated from the majority of the air as taught herein, then the majority of the heat release will not take place until the mixer (509). As long as the majority of the heat release occurs at or after mixer (509), the regenerative reactor will function at high efficiencies.

EXAMPLE 3

Autothermal Reforming ("ATR")

The controlled combustion reverse flow regenerative reactor may be employed for Autothermal Reforming ("ATR"). In the RTO application, the amount of oxidant (air) is conventionally many times greater than the amount needed for stoichiometric combustion of the contaminants and the supplemental fuel. Also, the incoming contaminated air is near ambient conditions of pressure and temperature. For ATR, the oxidant is present in sub-stoichiometric amounts, and may be absent of any diluents. The fuel is not a supplementary material, but a feedstock to be reformed. Pressures and feed temperature are typically substantially higher. These differences notwithstanding, the application includes substantially the same components as the RTO application and is illustrated in FIG. 5b. Preferably, the feed stream (504) in largest volume flow rate will be distributed into the majority of regenerative body (501) channels via the entry distribution volume (507). The feed stream (505) having lower volume flow rate is distributed via distributor (510) into select channels. The oxidant, fuel and optionally steam or CO2 are heated in regenerative body (501) and are mixed at the mixer (509) whereupon the exothermic autothermal reforming reactions occur. Reactions can be assisted by catalyst placed in all or part of the regenerative bodies (501 and 502). Reaction is substantially confined within the regenerative body (502) following the mixer, and cooling occurs within the regenerative body (502) following the mixer. Cool syngas is the product (506) of the reactor. Frequent flow reversal (via streams 504a, 505a, 506a) is used to keep the sensible heat (of heating or cooling) moving back and forth between the two bodies.

Although the invention has been described in detail herein, the skilled practitioner will recognize other embodiments of the invention that are within the scope of the claims.

What is claimed is:

1. A process for controlling the location of an exothermic reaction between two or more reactants in a cyclic reverse-flow reactor system comprising:
  (a) supplying the first reactant through a first channel means in a first regenerative bed and supplying at least a second reactant through a second channel means in the first regenerative bed,
  (b) combining said first and second reactants by a gas mixing means situated at an exit of the first regenerative bed and reacting the combined gas to produce a heated reaction product, wherein the cyclic reverse flow reactor system comprises a reaction zone having a volume A, a recuperation zone having a volume B, and a mixer zone having a volume C, whereby volume C is less than about twenty percent of a quantity that is volume A plus volume B plus volume C,
  (c) passing the heated reaction product through a second regenerative bed thereby transferring heat from the reaction product to the second regenerative bed.

2. The process of claim 1 wherein said cyclic reverse flow reactor system comprises a reaction zone and a recuperation zone, and a gas mixer means situated therebetween.

3. The process of claim 2 wherein the gas mixer means is constructed from material able to withstand temperatures in excess of about 600° C.

4. The process of claim 3 wherein the gas mixer means is constructed from material able to withstand temperatures in excess of about 1000° C.

5. The process of claim 4 wherein the gas mixer is constructed from material able to withstand temperatures in excess of about 1300° C.

6. The process of claim 1 wherein said first and second channel means axially traverse the first regenerative bed and pass the first and second gas to the gas mixer means.

7. The process of claim 6 wherein the gas mixer segment have axial cross sectioned areas that are about equal in area.

8. The process of claim 7 wherein the gas mixer segments include gas swirl means that function to mix gases flowing therethrough.

9. The process of claim 8 wherein gas from the first and second channel means flow into the gas mixer segments, combining therein, combusting and passing through the second regenerative beds.

10. The process of claim 9 wherein the gas from first and second channel means are each divided about equally among the gas miser segments.

11. The process of claims 2 or 9 wherein said combusting occurs proximate to an interface between the gas mixer means and the second regenerative bed.

12. The process of claim 11 wherein the gas mixer comprises a ceramic.

13. The process of claim 1 wherein volume C is less than about ten percent of the quantity of volume A plus volume B plus volume C.

14. The process of claim 1 wherein the gas mixer segments have an axial cross sectional area whose linear dimension is D, and an axial length L, the ratio of L to D ranges from about 0.1 to about 5.0.

15. The process of claim 14 wherein the gas mixer segments have an axial cross sectional area whose linear dimension is D, and an axial length L, the ratio of L to D ranges from about 0.3 to about 2.5.

16. The process of claim 15 wherein at least seventy-five percent of the reactant gases have not reacted in the first regenerative bed.

17. The process or claim 16 wherein the endothermic reaction of the cyclic reverse-flow reactor system comprises steam reforming, carbon dioxide reforming, pyrolysis, catalytic cracking, dehydrogenation, dehydration, or combinations thereof.

18. The process of claim 1 wherein said first and second channel means function to maintain said first and second reactants separated such that at least fifty percent of such gases have not reacted in the first regenerative bed while transiting the first regenerative bed.

19. The process or claim 1 wherein the cyclic reverse-flow reactor system is an asymmetric reaction chemistry system coupling the exothermic reaction with an endothermic reaction.

20. The process of claim 19 wherein the pyrolysis reaction comprises steam cracking reactions of ethane, naptha, gas oil or combinations thereof.

21. The process of claim 19 wherein the dehydrogenation reaction comprises alkane dehydrogenation, alkyl-aromatic dehydrogenation, or combinations thereof.

22. The process of claim 19 wherein the dehydration reaction comprises methanol dehydration, ethanol dehydration, or combinations thereof.

23. The process of claim 19 wherein the pyrolysis reaction includes hydropyrolysis reactions comprising methane hydropyrolysis to produce acetylene.

24. The process of claim 19 wherein the pyrolysis reaction comprises $H_2S$ pyrolysis.

25. The process of claim 1 wherein the first reactant is a fuel comprising CO, $H_2$, hydrocarbon(s), oxygenates, petrochemical, or a mixture thereof.

26. The process of claim 24 or 25 wherein the first reactant, or the second reactant, or both, further comprise non-combustible gas or gases.

27. The process or claim 26 wherein the exothermic reaction comprises lull oxidation or partial oxidation.

28. The process of claim 1 wherein the second reactant is an oxygen containing gas.

29. The process of claim 28 wherein the oxygen containing gas is air.

30. The process of claim 1 wherein the cyclic reverse flow reactor system is a symmetric reaction system.

* * * * *